US008090543B2

(12) United States Patent
Glanowski et al.

(10) Patent No.: US 8,090,543 B2
(45) Date of Patent: *Jan. 3, 2012

(54) COMPUTER ALGORITHM FOR AUTOMATIC ALLELE DETERMINATION FROM FLUOROMETER GENOTYPING DEVICE

(75) Inventors: Stephen A. Glanowski, Great Falls, VA (US); Jeremy Heil, Derwood, MD (US); Emily S. Winn-Deen, Livermore, CA (US); Ivy A. McMullen, Towson, MD (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/831,947

(22) Filed: Jul. 7, 2010

(65) Prior Publication Data

US 2011/0022555 A1 Jan. 27, 2011

Related U.S. Application Data

(63) Continuation of application No. 11/899,199, filed on Sep. 5, 2007, now abandoned, which is a continuation of application No. 10/085,142, filed on Mar. 1, 2002, now Pat. No. 7,272,506.

(51) Int. Cl.
*G06F 19/00* (2011.01)
(52) U.S. Cl. .............................................. 702/20; 435/6
(58) Field of Classification Search ........................ None
See application file for complete search history.

(56) References Cited

U.S. PATENT DOCUMENTS 6,223,127 B1 * 4/2001 Berno ............................. 702/19
2003/0054444 A1 * 3/2003 Battaglino et al. ............ 435/69.1

OTHER PUBLICATIONS

Gomes et al. (Ann. Hum. Genet., vol. 63, p. 535-538, 1999).*
Lindqvist et al., "Chromosome-specific Panels of Tri- and Tetranucleotide Microsatellite Markers for Multiplex Fluorescent Detection and Automated Genotyping: Evaluation of Their Utility in Pathology and Forensics" Genome Res., vol. 6, pp. 1170-1176, 1996.

* cited by examiner

*Primary Examiner* — Karlheinz R Skowronek

(57) ABSTRACT

The present invention provides methods and systems for an automated method of identifying allele values from data files derived from processed fluorophore emissions detected during the observation of fluorophore labeled nucleotide probes used in analyzing polymorphic DNA are provided. These methods are used in the rapid and efficient distinguishing of targeted polymorphic DNA sites without control samples.

11 Claims, 7 Drawing Sheets

COMPUTER ALGORITHM FOR AUTOMATIC ALLELE DETERMINATION FROM FLUOROMETER GENOTYPING DEVICE

This application is a continuation application of U.S. patent application Ser. No. 10/085,142, filed Mar. 1, 2002, which is incorporated herein in its entirety by reference.

FIELD OF THE INVENTION

The invention relates generally to the field of DNA genotypic analysis. More particularly, the invention relates to the allelic classification of DNA samples through cluster analysis of analyzed emission spectra observed from excited fluorophore-labeled nucleotide probes. Specifically, fluorophore-labeled nucleotide probes can be used verify DNA variations between individual samples and verify the expression of a region of DNA in different cell lines.

BACKGROUND OF THE INVENTION

Individual DNA sequence variations are known to directly cause specific diseases or conditions, or to predispose certain individuals to specific diseases or conditions. Such variations also modulate the severity or progression of many diseases. Additionally, DNA sequence variations exist between populations. Therefore, determining DNA sequence variations is useful for making accurate diagnoses, for finding suitable therapies, and for understanding the relationship between genome variations and environmental factors in the pathogenesis of diseases and prevalence of conditions.

There are several types of DNA sequence variations. These variations include insertions, deletions, restriction fragment length polymorphisms ("RFLPs"), short tandem repeat polymorphisms ("STRPs"), and single nucleotide polymorphisms ("SNPs"). Of these, SNPs are considered the most useful in studying the relationship between DNA sequence variations and diseases and conditions because they are more common, more stable, and more amenable to being employed in large-scale studies than other sorts of variations.

Currently, a set of over 3 million putative SNPs has been identified in the human genome. It is a current goal of researchers to verify these putative SNPs and associate them with phenotypes and diseases, eventually replacing currently-used RFLP and STRP linkage analysis screening sets. In order to successfully accomplish this goal, it will be necessary for researchers to generate and analyze large amounts of genotypic data.

A number of methods have been developed which can locate or identify SNPs. These methods include dideoxy fingerprinting (ddF), fluorescently labeled ddF, denaturation fingerprinting (DnF1R and DnF2R), single-stranded conformation polymorphism analysis, denaturing gradient gel electrophoresis, heteroduplex analysis, RNase cleavage, chemical cleavage, hybridization sequencing using arrays and direct DNA sequencing.

One method of particular relevance to the present invention employs a pair of fluorescent probes, each probe containing a different dye and specific for a different allele. In this method, the two probes are added to the DNA sample to be tested, and the mixture is amplified using PCR. If the DNA sample is homozygous for the first allele, the first probe's dye will exhibit a high degree of fluorescence and the fluorescence from the second probe's dye will be absent. Conversely, if the DNA sample is homozygous for the second allele, the second probe's dye will exhibit a high degree of fluorescence and the fluorescence from the first probe's dye will be absent. If the DNA sample is heterozygous for both alleles, then both probes should fluoresce equally. A commercial implementation of this method is APPLIED BIOSYSTEMS' TAQMAN platform, which employs APPLIED BIOSYSTEMS' PRISM 7700 and 7900HT SEQUENCE DETECTION SYSTEMS to record the fluorescence of each sample's PCR product.

A typical implementation generates amplification products from a set of a large number of samples at a time, and measures a pair of fluorescence values, one for each dye, from each amplified sample. To classify the samples, it is useful to first plot the fluorescence values of the entire set on a two dimensional graph, and observe that the plotted points tend to cluster into separate groups according to genotype, as illustrated in FIG. 1. In this figure, a human observer can readily discern that the data falls into four groups. The first group, in the lower-left hand corner, represents samples that had no amplification or were a no template control ("NTC") reaction. The second group, in the lower right hand corner, represents those samples homozygous for Allele 2. The third group, at the top, represents those samples homozygous for Allele 1. Finally, the fourth group, located between the second and third groups, represents the heterozygous samples. This classification is illustrated further in FIG. 2. Although it is relatively easy for human observer to analyze this type of data, it is necessary to develop a fast, reliable, and unsupervised method of computational analysis to produce the level of throughput necessary to analyze the large amounts of genotypic data generated.

Previous methods of computational analysis have employed a family of to algorithms known as clustering algorithms. A typical clustering algorithm receives raw unstructured data and processes it to form groups of data elements that are similar to each other. Clustering algorithms are well known in the field of computer science, and are typically applied in data mining applications. In a data mining application, clustering is used to identify relationships in data collections not readily observable to an expert user due to the volume of information.

A typical clustering algorithm examines the distance between data elements to find a common centroid. The centroid is mean of the value of the data elements belonging to a cluster. Clusters are selected by the algorithm to minimize the distance between the elements contained within it relative to the elements contained in other clusters. Clustering algorithms belong to the greater class of unsupervised machine learning algorithms. Other supervised machine learning algorithms, including decision trees and neural networks, were considered for application to analyzing output from a fluorometric genotyping device. However, all machine learning algorithms considered were determined to be insufficient to analyze this type of data accurately. A thorough review of initial collection of 80 human reviewed outputs revealed characteristics of the data that would not allow standard machine learning algorithms to work with a high degree of accuracy.

It is an object of this invention to provide a fast, accurate, and unsupervised method of classifying genotypic samples based on fluorometric data generated from them.

SUMMARY OF THE INVENTION

In one aspect, the invention relates to a method for categorizing the members of a dataset into discrete categories. In this aspect the dataset has a plurality of datapoints, and each datapoint has at least two numerical values associated with it. In this aspect, the method has the following steps: Assign each datapoint an angular value based on that datapoint's numerical values; sort the dataset by angular value; calculate the differences between adjacent angular values in the sorted dataset; determining category-dividing values by identifying differences that are larger than a predetermined threshold; and classifying datapoints according to their angular values relative to the category-dividing values.

In a further aspect, each datapoint has exactly two numerical values, and the angular value is an arctangent of the datapoint's numerical values. In a further aspect the numerical values are normalized before the angular values are calculated.

In a further aspect, the numerical values represent fluorometric data, wherein the different numerical values for each datapoint represent the fluorescence of a different dye.

In a further aspect, the method identifies exactly two category-dividing values and three categories. In a further aspect, these three categories represent homozygosity for a first allele, homozygosity for a second allele, and heterozygosity for both alleles.

In a further aspect the fluorometric data is measured from the product of an amplification reaction, and the method includes a step for removing datapoints that represent either a control reaction or a failure to amplify. In this aspect, the datapoints whose Euclidean distance falls beneath a predetermined threshold are removed from any further classification.

In a further aspect, the results of the classification are examined to determine whether to bring them to the attention of a human user. In this aspect, the results are examined for conditions that indicate that the classification was unsuccessful. Such conditions include excess classification in one category; classification into more than three categories, absence or near absence of any classification in one or more categories, unclassified datapoints, inadequate separation from control or nonamplification reactions, clusters having angular values that are either too high or too low, clusters whose ranges of angular values are too wide, classification that is not compatible with a Hardy-Weinberg equilibrium, and control or nonamplification reactions that are too far from the origin.

DETAILED DESCRIPTION OF INVENTION

Figure 1:
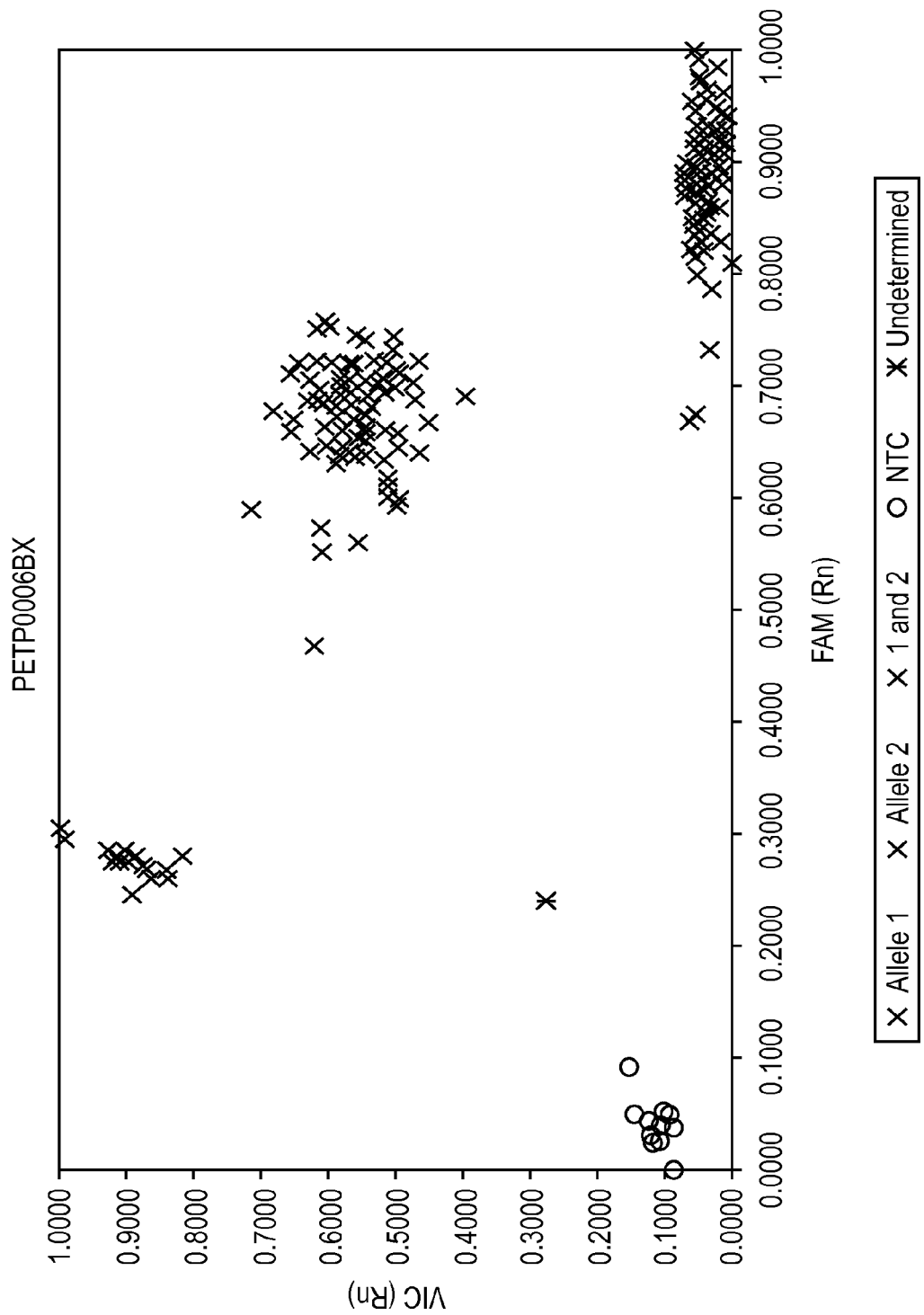
FIG. 1 provides a two dimensional scatterplot of fluorometric data.
Figure 2:
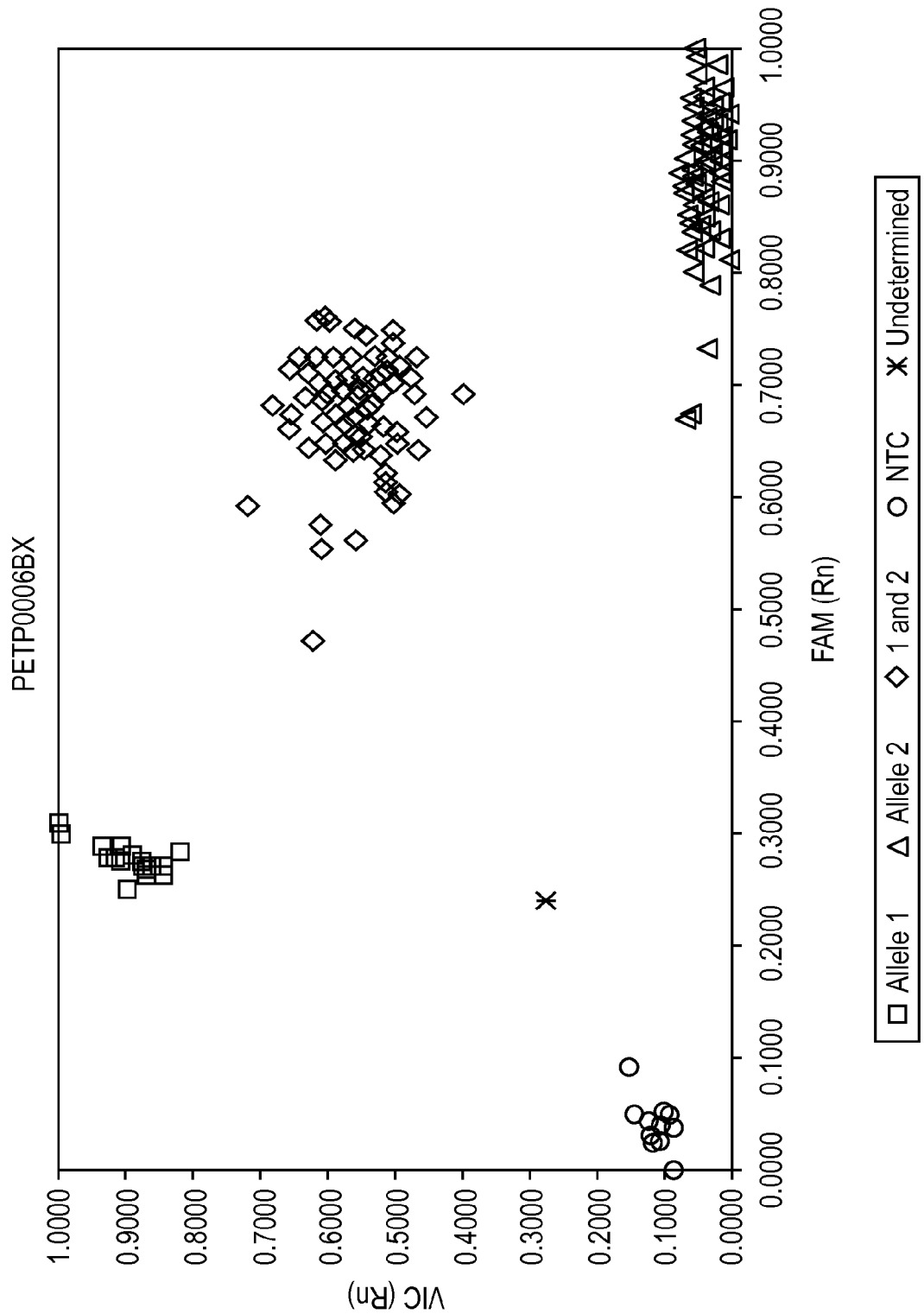
FIG. 2 provides a two dimensional scatter plot of fluorometric data classified by allele.
Figure 3:
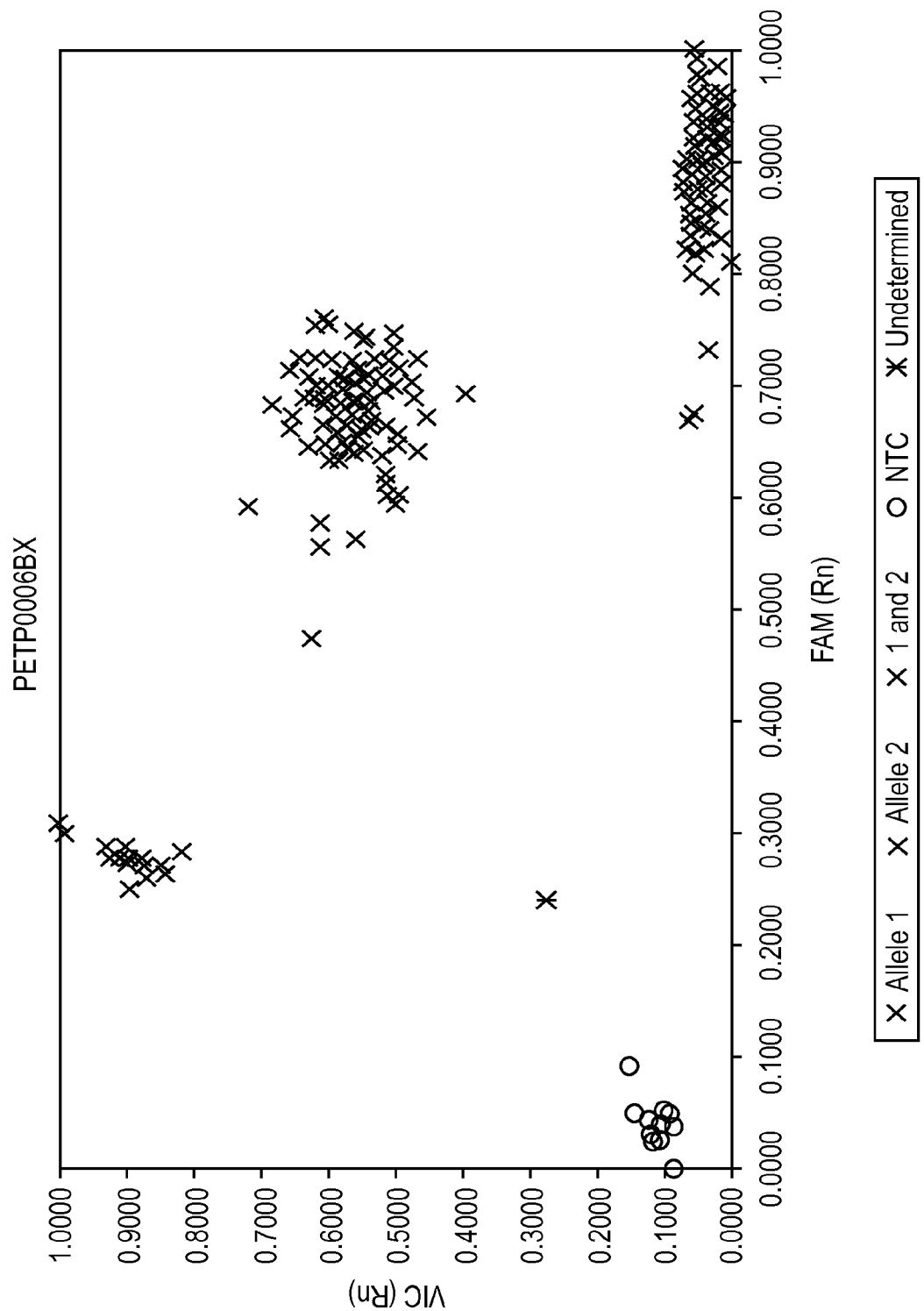
FIG. 3 provides a two dimensional scatterplot of raw fluorometric data.
Figure 4:
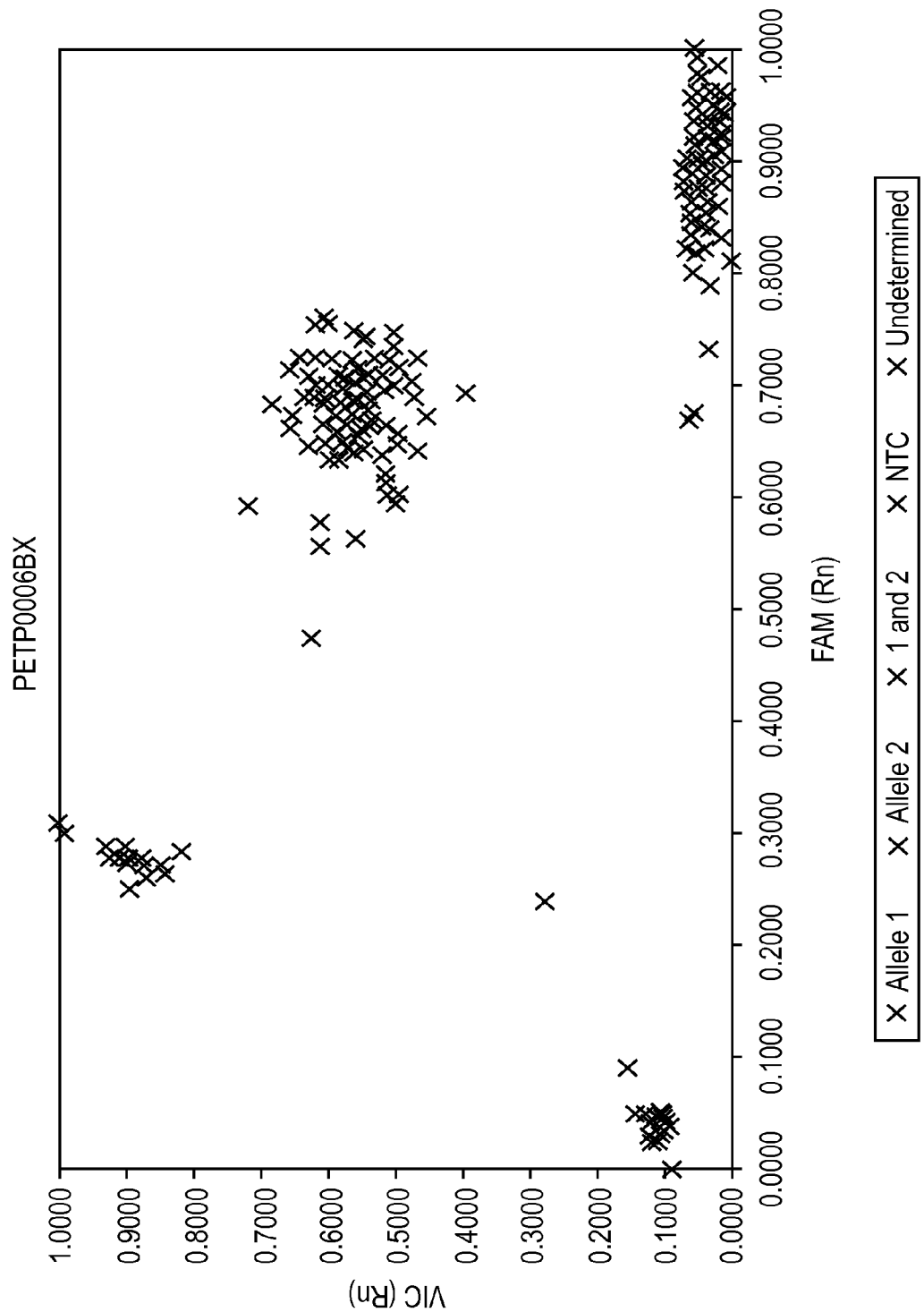
FIG. 4 provides a two dimensional scatterplot of normalized fluorometric data.
Figure 5:
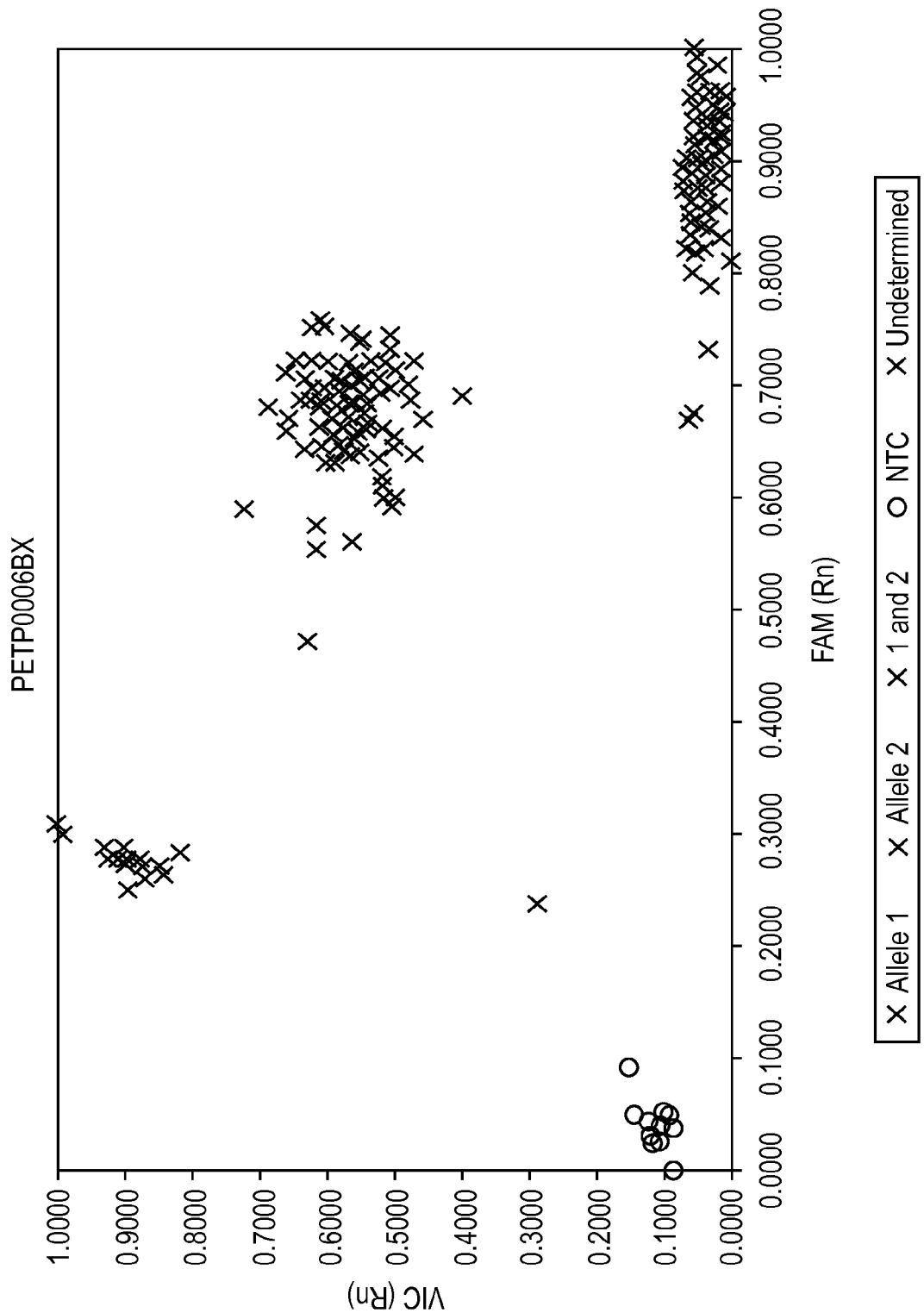
FIG. 5 provides a two dimensional scatterplot of normalized fluorometric data classified by allele.
Figure 6:
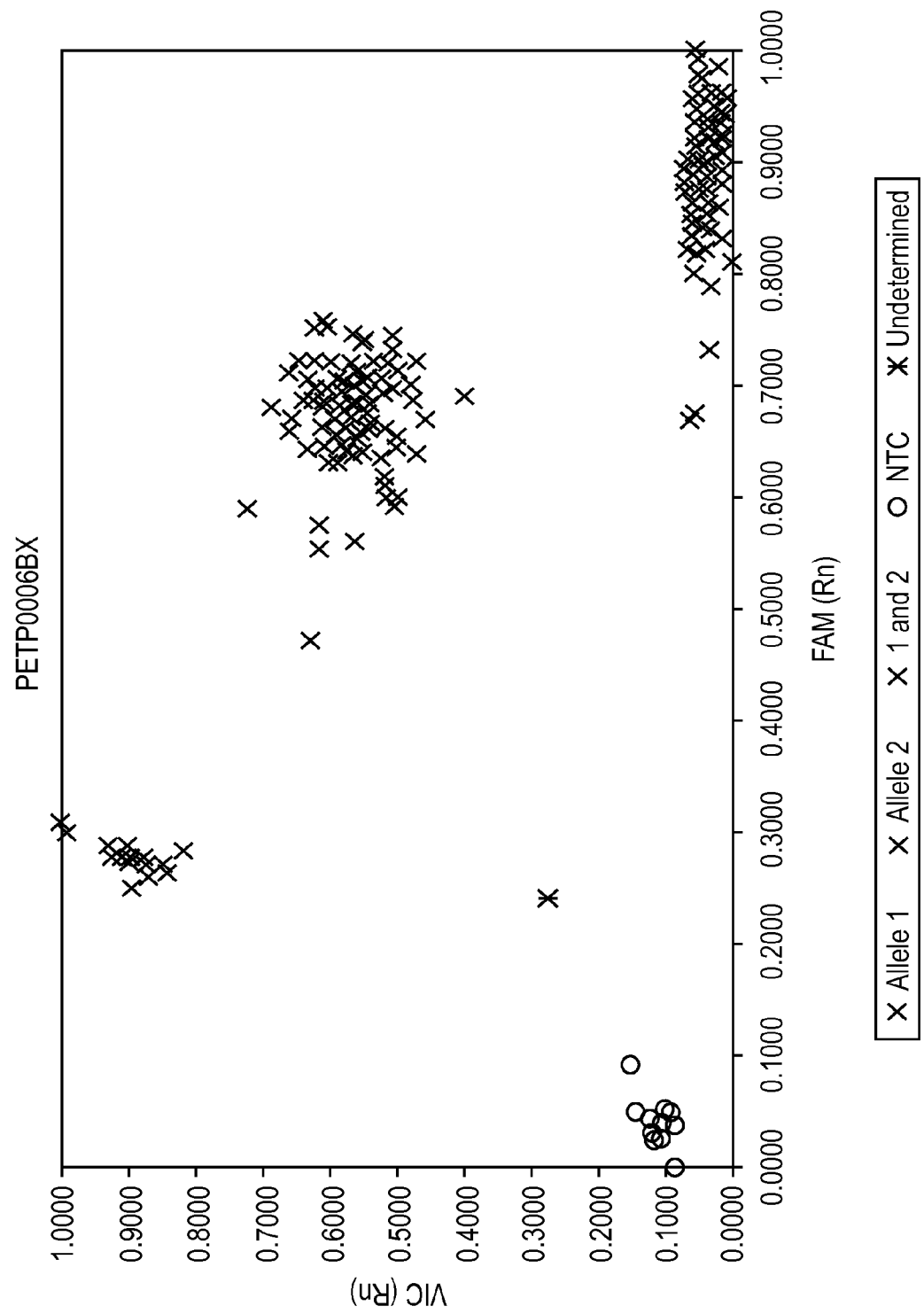
FIG. 6 provides a two dimensional scatterplot of normalized fluorometric data classified by allele, and undetermined datapoints identified.

Although the methods of the current invention can be used to classify any kind of bivariate or multivariate data, they are particularly useful for classifying genotypic data, especially allelic data generated by fluorescence.

In one embodiment, the fluorometric genotyping device generates for each sample a unique sample identifier, a value from one of the sample's fluorometric probes, and a value from the sample's other fluorometric probe. The paired fluorescence values can then be plotted as x and y values on a two-dimensional grid. Ideally, the data generated in this fashion should yield heterozygous datapoints in the upper-right quadrant, and homozygous datapoints for each allele in the upper-left and lower-right quadrants, respectively. If that were the case, then allele calling would be a simple matter of dividing the grid by quadrants. However, fluorometric genotypic has been observed to exhibit several characteristics and idiosyncrasies that must be addressed in order for an automated allele caller to function accurately, and have not been adequately addressed by previous methods of clustering and machine learning.

Traditional machine learning algorithms such as decision trees and neural networks generate solutions by training on a given collection of data where the outcome is known and then applying the trained system to predict data in unknown outcomes. Training these algorithms with fluorometric data produces a solution where a set of X and Y boundaries are defined that had the highest probability of being correct. However, the predictions of results that deviate from the trained form would have poor accuracy. Because fluorometric data tends to vary from instance to instance, a trained system is too rigid to be sufficiently accurate to operate unsupervised on a large number of samples.

Another imperfection of fluorometric data is that outputs from fluorometric genotyping devices can validly produce one to three clusters, in addition to clusters formed by samples that had no amplification or no template control reactions ("NTCs"). In general, fluorometric genotyping devices are expected to produce three clusters, but can validly produce only one or two. For example, if three clusters are expected but only two valid clusters are produced, then the datapoints could be invalidly categorized into three clusters. Clustering algorithms are generally given a fixed number of expected clusters, and any deviation from the expected number of clusters greatly reduces their effectiveness.

Another imperfection of fluorometric data is that datapoints belonging to the same category can be spread out spatially. A widely-spread cluster is usually observed for the category of heterozygous genotypes, where both fluorometric probes are active. A widely-spread cluster greatly reduces the effectiveness of clustering algorithms, especially when the distance between the furthest datapoints of a cluster and its centroid is greater than their distance to other clusters. Furthermore, as noted above, the number of valid clusters produced by fluorometric data can vary from the expected three to one or two. For example if two valid clusters are produced and one of them is widely-spread, it is likely that a clustering algorithm will incorrectly divide that one valid cluster into two invalid clusters.

In one embodiment, the dataset has a plurality of datapoints, and each datapoint has two numerical values associated with it. In an alternate embodiment, each datapoint has more than two numerical values associated with it. In a further embodiment, the numerical values represent quantitative empirical data In yet a further embodiment, the quantitative empirical data is measured fluorescence. In a further embodiment, the numerical values are normalized before being used in any subsequent calculations.

In this embodiment, an angular value is calculated for each datapoint in the dataset based upon the datapoint's numerical values. In a further embodiment, the angular value is an arctangent of the numerical values. The dataset is then sorted by angular value. A difference value is then calculated for each datapoint by subtracting the angular value of the previous datapoint from that of the current datapoint. The difference value of the first datapoint is that point's angular value.

Figure 7:
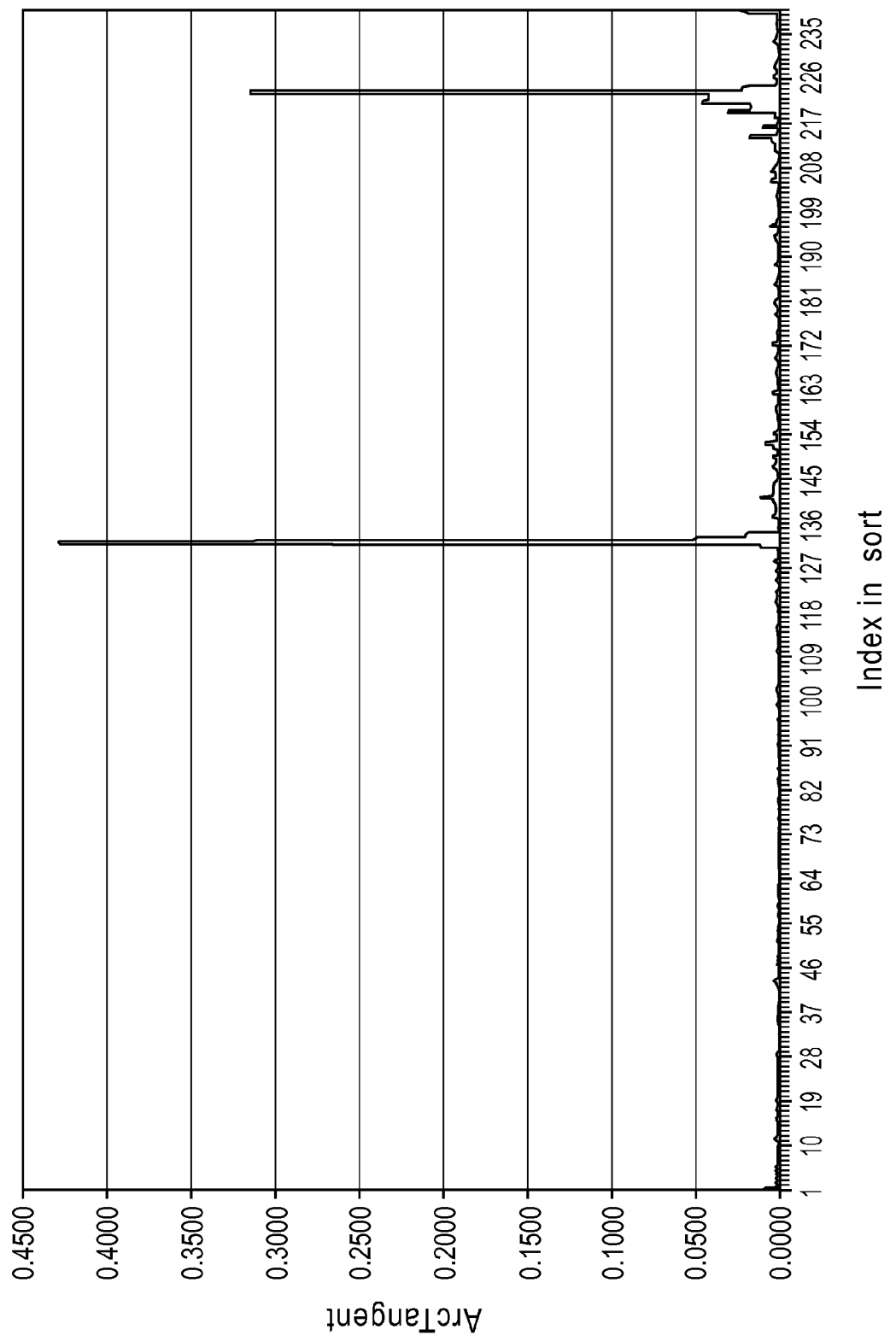
FIG. 7 provides a bargraph of the differences in arctangent values between adjacent datapoints sorted by arctangent.

If the difference value is large enough to exceed a predetermined threshold, a new category-dividing value is designated between the two angle values from which that difference value was calculated. In one embodiment, the category-dividing value is the average of the two angle values from which the above-threshold difference value was calculated. FIG. 7 illustrates the difference values for an example dataset. In this example, the samples are lined along the X-axis according to the rank of their angular value, and each sample's difference value is plotted on the Y-axis. As illustrated in FIG. 7, the results indicate the presence of two difference values which stand out dramatically from the rest of the data. Two dividing values are designated, one between sorted samples 131 and 132 and the other between sorted samples 222 and 223, each at a angle value between the two angle values which generated the above-threshold difference value.

As their name suggests, the category-dividing values are subsequently used to separate datapoints into categories. In this example, sorted datapoints 1-131 are classified as homozygous for a first allele, sorted datapoints 132-222 are classified as heterozygous, and samples 223-239 are classified as homozygous for a second allele.

The data contained in the example illustrated in FIG. 7 and described above are relatively clean and well-adapted to machine analysis. In one embodiment, the data are examined for conditions which indicate that the data are less well-formed and may not yield correct results when subjected to unsupervised machine analysis. In a further embodiment, if such conditions are detected, the method adapts its analysis to the idiosyncrasies of the dataset in order to yield a more accurate analysis. In yet a further embodiment, if such conditions are detected the dataset is flagged to indicate that it should be examined by a human reviewer.

In one embodiment, the data are examined to determine if control samples are present in the dataset. In a further embodiment, identified control samples are removed from the dataset before any further classification is performed.

In one embodiment, the range between the maximum and minimum observed values for each fluorophore-labeled nucleotide probe is calculated. If the range falls below a predetermined threshold, it is determined that the results are only valid for the other probe. Those samples producing data with the valid probe are then distinguished from samples that had no amplification or were NTCs. In one embodiment, all datapoints within a predetermined distance from the minimum observed values of the dataset are determined to be NTCs and the remaining datapoints are classified as belonging to the observed probe.

If, on the other hand, the range between maximum and minimum observed values for each fluorophore-labeled nucleotide probe exceeds the predetermined threshold, it is determined that multiple clusters are probably present, and the following steps are taken: All of the numerical values are normalized. In a further embodiment, all of the numerical values are normalized on a scale ranging from 0.0 to 1.0. Then the Euclidean distance between minimum values and each sample is computed. Samples are predicted as NTC or non-amplification and removed from further consideration if their distance to minimum values fall below a predetermined distance threshold.

The average distance of all remaining datapoints is then computed and used to calculate a threshold. All remaining datapoints that fall below this threshold are predicted as undetermined and removed from further classification.

Once the above-described screening steps are performed, the method of this embodiment proceeds similarly to that of the previous example: Angular values are calculated for each datapoint; the dataset is sorted by angular value; difference values are calculated; category-dividing values are identified; and each datapoint is categorized according to its angular value.

In one embodiment, the classification results are then examined with a series of evaluations to determine if there are any characteristics to bring to the attention of a human reviewer. Examples of such conditions include excess classification in one category, classification into more than three categories, absence or near absence of any classification in one or more categories, unclassified datapoints, inadequate separation from control or nonamplification reactions, clusters having angular values that are either too high or too low, clusters whose ranges of angular values are too wide, classification that is not compatible with a Hardy-Weinberg equilibrium, and control or nonamplification reactions that are too far from the origin.

If the samples were identified as all homozygous, it not considered an error of the clustering algorithm, but needs to be noted to the investigator that the assay is not variable.

If only one cluster was identified and it could not be determined to be all homozygous then the dataset is flagged to indicate that human review is recommended.

If more than three clusters were identified then the dataset is flagged so that a human user can review the calls.

If more than a preset number of datapoints are predicted as undetermined then the dataset is flagged indicating that human review is desired. In a further embodiment, this preset number is 4.

If the samples from a probe are not separated from the node template controls by a threshold distance determined by the probe technology used then the dataset is flagged to indicate that the probe is producing a weak signal.

If the heterozygosity of the predicted calls is greater than a given heterozygosity threshold then the dataset is flagged so that a human user can review the predicted results. Heterozygosity is the predicted number of heterozygous sample divided by the number of heterozygous and homozygous samples.

If the homozygous cluster for a first allele is below an arctangent of 1.0 then the dataset is flagged indicating that the cluster is in too low of a position and should be human reviewed.

If the homozygous cluster for a second allele is above an arctangent of 0.67 then the database is flagged indicating that the cluster is in too high of a position and should be human reviewed.

If the heterozygous cluster is above an arctangent of 1.35 then the database is flagged indicating that the cluster is in too high of a position and should be human reviewed. Similarly, if the heterozygous cluster is below an arctangent of 0.18 then the database is flagged indicating that the cluster is in too low of a position and should be human reviewed.

If there are three clusters and the cluster with the smallest number of samples, also known as the minor allele cluster, is greater then the heterozygous cluster then these results do not agree with population genetics Hardy-Weinberg principle and the database is flagged so that a human will review the results.

If any cluster is wider then 0.6 from the start of the cluster's arctangent to its end then the cluster is unusually wide and the dataset is flagged to have the results human reviewed.

If the center of the predicted node template control cluster is greater then 0.3 on a probe axis in a 0.0 to 1.0 normalized coordinate system, this indicates a problem with the probe and the dataset is flagged so the results are human reviewed.

EQUIVALENTS

The invention may be embodied in other specific forms without departing from the spirit or essential characteristics thereof. The foregoing embodiments are therefore to be considered in all respects illustrative, rather than limiting, of the invention described herein. Scope of the invention is thus indicated by the appended claims, rather than by the foregoing description, and all variants which fall within the meaning and range of equivalency of the claims are therefore intended to be embraced therein.

What is claimed:

1. A method for categorizing a dataset comprising a plurality of datapoints, comprising: receiving a plurality of datapoints generated by a fluorometric sequence detection instrument, wherein the plurality of data points correspond to a plurality of amplified samples;
   generating a plurality of angular values by calculating an angular value for each datapoint based on numerical values of each data point;
   generating a plurality of angular difference values by calculating differences between adjacent angular values;
   determining at least one category-dividing value by identifying at least one angular difference value of the plurality of angular difference values above a predetermined threshold gap value;
   classifying at least one datapoint according to its angular value relative to at least one category-dividing value; and
   providing a classification result based at least in part on the at least one category-dividing value.

2. The method of claim 1 wherein each datapoint comprises two numerical values.

3. The method of claim 2 wherein the angular value is an arctangent of the two numerical values.

4. The method of claim 1 wherein the numerical values comprise fluorometric data.

5. The method of claim 1 wherein the determining identifies two category-dividing values comprising a first and a second category-dividing value.

6. The method of claim 1 further comprising normalizing the numerical values to a scale.

7. The method of claim 6 wherein the scale ranges from 0.0 to 1.0.

8. The method of claim 1 further comprising removing non-amplification datapoints from the dataset, comprising:
   calculating a Euclidean distance for each datapoint; and
   removing at least one datapoint from the dataset, wherein the Euclidean distance of the datapoint falls below a predetermined distance threshold.

9. The method of claim 5 wherein the classifying the at least one datapoint further comprises:
   classifying at least one datapoint in a first category, wherein all datapoints of the first category have an angular value lower than the first and second category-dividing values;
   classifying at least one datapoint in a second category, wherein all datapoints of the second category have an angular value between the first and second category-dividing values; and
   classifying at least one datapoint in a third category, wherein all datapoints of the third category have an angular value greater than the first and second category-dividing values.

10. The method of claim 9 wherein classification in the first category corresponds to homozygosity for a first allele, classification in the third category corresponds to homozygosity for a second allele, and classification in the second category corresponds to heterozygosity for the first and second alleles.

11. The method of claim 10 further comprising determining the presence of a condition to bring to the attention of a human user, wherein the condition comprises the proportion of datapoints classified as heterozygous exceeding a predetermined threshold.

* * * * *